(12) United States Patent
Nystrom

(10) Patent No.: US 9,390,632 B2
(45) Date of Patent: Jul. 12, 2016

(54) SIMULATED CONTRAST INJECTION MEDIUM

(71) Applicant: ACIST Medical Systems, Inc., Eden Prairie, MN (US)

(72) Inventor: Sidney D. Nystrom, Shoreview, MN (US)

(73) Assignee: ACIST MEDICAL SYSTEMS, INC., Eden Prairie, MN (US)

( * ) Notice: Subject to any disclaimer, the term of this patent is extended or adjusted under 35 U.S.C. 154(b) by 50 days.

(21) Appl. No.: 14/547,393

(22) Filed: Nov. 19, 2014

(65) Prior Publication Data

US 2015/0073274 A1   Mar. 12, 2015

Related U.S. Application Data

(62) Division of application No. 13/670,177, filed on Nov. 6, 2012, now Pat. No. 8,915,399.

(51) Int. Cl.

| | |
|---|---|
| *B67B 7/00* | (2006.01) |
| *G09B 23/28* | (2006.01) |
| *A61M 5/145* | (2006.01) |
| *C08L 29/04* | (2006.01) |
| *A61K 49/00* | (2006.01) |

(Continued)

(52) U.S. Cl.
CPC .......... *G09B 23/286* (2013.01); *A61K 49/0002* (2013.01); *A61M 5/007* (2013.01); *A61M 5/1456* (2013.01); *A61M 5/14216* (2013.01); *A61M 5/14228* (2013.01); *A61M 5/14546* (2013.01); *A61M 5/14566* (2013.01); *A61M 5/172* (2013.01); *A61M 5/178* (2013.01); *A61M 25/00* (2013.01); *C08L 29/04* (2013.01); *G09B 23/285* (2013.01); *A61M 2205/3331* (2013.01); *A61M 2205/50* (2013.01); *A61M 2205/70* (2013.01); *A61M 2209/02* (2013.01)

(58) Field of Classification Search
CPC ..................... A61M 5/14546; A61M 5/14566; A61M 5/1456; A61M 5/16827; A61M 5/20; A61M 5/007; A61M 5/172; A61M 5/14228; A61M 5/14216; A61M 2205/70; A61M 2205/3331; A61M 2205/50; A61M 2209/02; A61M 25/00; G09B 23/268; G09B 23/285; A61K 49/0002; C08L 29/04
USPC ........ 222/1, 63, 503, 261–263, 258; 600/432, 600/431, 416; 604/154, 151, 131, 228
See application file for complete search history.

(56) References Cited

U.S. PATENT DOCUMENTS

| | | |
|---|---|---|
| 5,527,926 A | 6/1996 | Ranganathan et al. |
| 5,620,425 A | 4/1997 | Heffernan et al. |

(Continued)

*Primary Examiner* — Lien Ngo

(74) *Attorney, Agent, or Firm* — Fredrikson & Byron, P.A.

(57) ABSTRACT

A medical fluid injection system may include a powered injector and a fluid reservoir that contains a simulated contrast medium. The simulated contrast medium may exhibit a fluid flow property substantially equal to that of an active contrast medium but be devoid of any active contrast agent that provides contrast during diagnostic imaging. During operation, a syringe in the powered injector may be filled with the simulated contrast medium and then evacuated to discharge the simulated contrast medium from the syringe. The simulated contrast medium may be used to test and evaluate the performance of the powered injector prior to use in a medical procedure without exposing personnel to an active contrast agent or creating medical waste that contains the active contrast agent.

20 Claims, 15 Drawing Sheets

(51) Int. Cl.
*A61M 5/00* (2006.01)
*A61M 5/172* (2006.01)
*A61M 5/178* (2006.01)
*A61M 25/00* (2006.01)
*A61M 5/142* (2006.01)

(56) References Cited

U.S. PATENT DOCUMENTS

| | | | |
|---|---|---|---|
| 5,806,519 A | 9/1998 | Evans, III et al. | |
| 6,099,502 A | 8/2000 | Duchon et al. | |
| 6,269,340 B1 | 7/2001 | Ford et al. | |
| 6,290,682 B1 | 9/2001 | Myers | |
| 6,951,641 B2 | 10/2005 | Lasser | |
| 7,128,729 B2 | 10/2006 | Duchon et al. | |
| 7,389,788 B2 | 6/2008 | Wilson et al. | |
| 7,477,929 B2 | 1/2009 | Klotz et al. | |
| 7,753,885 B2 * | 7/2010 | Duchon | A61B 6/481 600/432 |
| 7,862,340 B2 | 1/2011 | Chen et al. | |
| 8,066,970 B2 | 11/2011 | Wynn et al. | |
| 8,079,999 B2 * | 12/2011 | Duchon | A61M 5/14216 600/432 |
| 8,403,909 B2 | 3/2013 | Spohn et al. | |
| 8,613,730 B2 | 12/2013 | Hieb et al. | |
| 2005/0277096 A1 * | 12/2005 | Hendrickson | G09B 23/285 434/262 |
| 2006/0079768 A1 * | 4/2006 | Small | A61M 5/14546 600/432 |
| 2006/0083687 A1 * | 4/2006 | Yang | A61B 5/0263 424/9.3 |
| 2006/0188138 A1 | 8/2006 | Kohler et al. | |
| 2006/0235297 A1 | 10/2006 | Kawamoto | |
| 2009/0149743 A1 | 6/2009 | Barron et al. | |
| 2010/0004909 A1 | 1/2010 | Nitz | |
| 2010/0185040 A1 | 7/2010 | Uber et al. | |
| 2012/0130236 A1 * | 5/2012 | Nystrom | A61M 5/007 600/432 |
| 2013/0123619 A1 * | 5/2013 | Griggs | A61M 5/007 600/432 |
| 2013/0338587 A1 | 12/2013 | Nystrom et al. | |
| 2014/0094680 A1 | 4/2014 | Kowarschik et al. | |

* cited by examiner

SIMULATED CONTRAST INJECTION MEDIUM

This application is a divisional of U.S. patent application Ser. No. 13/670,177, filed Nov. 6, 2012, the entire contents of which are incorporated herein by reference.

TECHNICAL FIELD

This disclosure relates to injectable contrast media and, more particularly, to simulated injectable contrast media for testing medical equipment.

BACKGROUND

Contrast media are used in medical settings to enhance the visibility of bodily structures during imaging procedures. Contrast media can highlight features that would otherwise be less distinguishable from nearby tissue to help a clinician diagnose and treat a patient's medical condition. A patient is typically injected with a contrast medium before or during an imaging procedure and then exposed to radiation or electromagnetic energy to generate an image of the patient's body. Example imaging techniques include X-ray, computed tomography (CT), nuclear magnetic resonance (NMR)/magnetic resonance (MR), ultrasound, fluoroscopy, and positron emission tomography (PET).

As an example, angiography is a medical procedure that usually involves injecting a patient with a contrast medium. Angiography is a procedure used in the diagnosis and treatment of cardiovascular conditions including abnormalities or restrictions in blood vessels. During angiography, a radiographic image of the heart or a vascular structure is obtained by injecting a radiographic contrast medium through a catheter into a vein or artery. The injected contrast medium can pass to vascular structures in fluid communication with the vein or artery in which the injection is made. X-rays are then passed through the region of the body in which the contrast material was injected. The X-rays are absorbed by the contrast medium, causing a radiographic outline or image of the blood vessel containing the contrast material.

When used, a contrast medium is typically injected into a patient by an automated injection system. While the apparatus for injecting the contrast medium can vary, most systems include a syringe operatively connected with a catheter. The catheter is placed into a vein or artery of a patient. During operation, a ram forces the contrast medium out of the syringe, through the catheter, and into the patient at a rate and volume determined by the speed of movement of the ram.

To ensure that an automated injection system is working properly prior to being placed in service and even after being placed in service, a contrast medium may be periodically passed through the injection system without actually injecting the contrast medium into a patient. Rather, the contrast medium may be passed through the injection system to monitor and validate the operational integrity of the injection system without injecting the contrast medium into a patient. For example, the fluid integrity of various fluid reservoirs, fluid lines, and connectors may be monitored during a test injection to ensure that there are no leaks in the injection system. The contrast medium discharged from an injection system during such operational testing is typically discarded after use.

Medical contrast media are generally expensive to manufacture and chemically stable once discarded. For example, some medical contrast media may pass through waste water treatment plants without decomposing. Ensuring that medical injection systems can be accurately tested and validated while limiting consumption of contrast media to medical procedures may provide a variety of benefits.

SUMMARY

In general, this disclosure is directed to systems and techniques for developing simulated contrast media and for operating medical fluid delivery devices using the simulated contrast media. A simulated contrast medium may be a liquid that simulates the fluid flow properties of a traditional contrast medium introduced into a patient during an imaging procedure but which does not contain active contrast agents. For example, a simulated contrast medium may exhibit fluid flow properties substantially equal to a contrast medium containing an active contrast agent that enhances the visual contrast of structures or fluids within a body during an imaging procedure. However, the simulated contrast medium may be devoid of any active contrast agents such that, were the simulated contrast medium injected into the body of a patient, the simulated contrast medium would not enhance the contrast of any structures or fluids within the body of the patient during an imaging procedure. Of course, a clinician would not actually inject the simulated contrast medium into a patient during hardware testing. By replicating the fluid flow properties of a contrast medium that contains an active contrast agent, the simulated contrast medium may imitate the flow behavior and injection characteristic of the contrast medium. Accordingly, the simulated contrast medium can be used to reliably test and validate the operational integrity of an injection system and related hardware/software. Yet because the simulated contrast medium does not contain an active contrast agent, the simulated contrast medium can be handled without exposing workers to the active contrast agent and disposed of without introducing the active contrast agent into the environment.

In one example, a system is described that includes a powered injector, a fluid reservoir, and a processor. The powered injector includes a plunger, a motor configured to advance and retract the plunger, and a syringe holder configured to hold a syringe so that the plunger moves within the syringe. The fluid reservoir contains a simulated contrast medium in fluid communication with the syringe. According to the example, the simulated contrast medium exhibits a fluid flow property equivalent to that of an active contrast medium but is devoid of any active contrast agent that provides contrast during diagnostic imaging. The processor is configured to retract the plunger within the syringe so as to draw the simulated contrast medium from the reservoir into the syringe and advance the plunger within the syringe so as to discharge the simulated contrast medium from the syringe.

In another example, a method is described that includes connecting a fluid reservoir containing a simulated contrast medium to a syringe of a powered injector. The simulated contrast medium exhibits a fluid flow property equivalent to that of an active contrast medium but is devoid of any active contrast agent that provides contrast during diagnostic imaging. The example method also includes performing a fill operation by moving, under the control of a processor, a plunger of the powered injector rearward to draw the simulated contrast medium from the fluid reservoir into the syringe. The example method further includes performing an injection operation by moving, under the control of the processor, the piston of the powered injector forward to discharge the simulated contrast medium from the syringe.

In another example, a method is described that includes injecting, under the control of one or more processors, a contrast medium through a catheter so as to generate data indicative of a pressure of the contrast medium versus time and injecting, under the control of the one or more processors, a simulated contrast medium through the catheter so as to generate data indicative of a pressure of the simulated contrast medium versus time. The simulated contrast medium includes a simulated contrast agent and a diluent. According to the example, the method further includes comparing, by the one or more processors, the pressure of the contrast media to the pressure of the simulated contrast media and adjusting a concentration of the simulated contrast agent in the simulated contrast media based on the comparison.

The details of one or more examples are set forth in the accompanying drawings and the description below. Other features, objects, and advantages will be apparent from the description and drawings, and from the claims.

DETAILED DESCRIPTION

Figure 1:
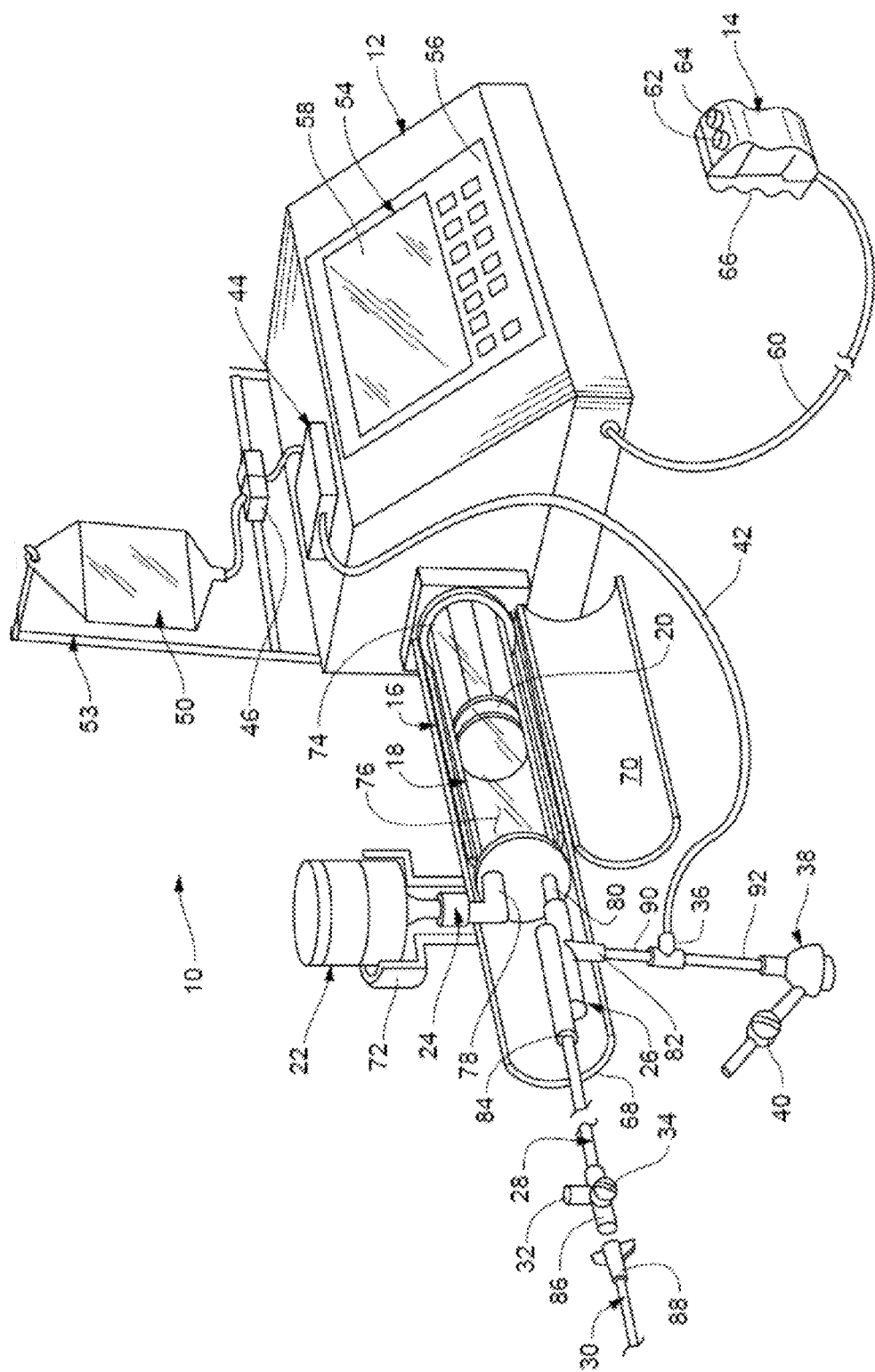
FIG. 1 is a perspective view of example medical fluid injection system.

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes may be provided for selected elements, and all other elements employ that which is known to those of skill in the field of the invention. Those skilled in the art will recognize that many of the examples provided have suitable alternatives that can be utilized.

A powered medical fluid injector may be used to inject a contrast medium into the body of a patient during a diagnostic imaging procedure. The contrast medium may contain an active contrast agent that interacts with radiation or electromagnetic energy from a diagnostic imaging machine to enhance the visual contrast of structures or fluids within a body of the patient, for example, as compared to structures or fluids not exposed to the contrast agent. For example, the contrast agent may highlight features that would otherwise be less distinguishable from nearby tissue to help a clinician diagnose and treat a patient's medical condition.

To ensure that a powered medical fluid injector and/or related hardware are operating properly prior to being placed in service and, in some applications, even after being placed in service, the injector and/or related hardware may be tested by filling the injector with contrast medium and then operating the injector to discharge the contrast medium from the injector. Unlike injection during a diagnostic imaging procedure, however, the contrast medium is not discharged from the injector into a patient. Instead, the contrast medium is discharged from the injector into a waste receptacle. The test injection may be used to confirm that various components of the injector such as a motor and gears are operating properly and that the fluid connections in the injector provide fluid integrity for the system. The test injection may also be used to confirm that tubing lines (e.g., part of a patient-specific tubing kit) are fluid tight and can withstand fluid pressures generated during an injection procedure.

While contrast medium with an active contrast agent can be used to test the performance of an injector and related hardware outside of a medical procedure, use of the contrast medium may expose test personnel to the active agent and create waste that is difficult to dispose of. In some examples, this disclosure describes systems and techniques that employ a simulated contrast medium for testing a powered medical fluid injector and related hardware. The simulated contrast medium may exhibit fluid flow properties equivalent to that of an active contrast medium but be devoid of any active contrast agent that provides contrast during diagnostic imaging. For example, the simulated contrast medium may be configured such that, were the simulated contrast medium injected into a patient, the simulated contrast medium would not cause a contrast between structures or fluids infused with the simulated contrast medium and adjacent structures or fluids not infused with the simulated contrast medium.

By replicating the fluid flow properties of the active contrast medium, an injector using the simulated contrast medium may exhibit operational performance similar to how the injector would perform, were the injector using the active contrast medium. Further, because the simulated contrast medium does not contain active contrast agent, the simulated contrast medium may be handled and disposed of without the risks associated with the active contrast medium.

To develop a simulated contrast medium for a particular application, a contrast medium with an active contrast agent may first be passed through a powered injector to develop fluid flow characteristic data for the medium. Thereafter, a working formulation of the simulated contrast medium may be passed through the powered injector to develop corresponding fluid flow characteristic data for the working formulation of the simulated contrast medium. After comparing the fluid flow characteristic data of the working formulation of the simulated contrast medium to the fluid flow characteristic data of the active contrast medium, the composition of the simulated contrast medium may be adjusted until its fluid flow characteristics are substantially equal to that of the active contrast medium. In this manner, a simulated contrast medium may be produced that exhibits one or more fluid flow properties substantially equal to that of the active contrast medium.

Example systems and methods for formulating a simulated contrast medium are described in greater detail below with respect to FIGS. 6-9. However, an example system that includes a powered injector that may inject a simulated contrast medium will first be described with reference to FIGS. 1-5.

FIG. 1 is a perspective illustration of an example contrast medium injector system 10, which may be used to inject contrast medium into a patient under interactive physician control during a medical procedure, such as an angiogram. As described in greater detail below, contrast medium injector system 10 may also be used to inject a simulated contrast medium, e.g., to test and validate the operational integrity of the system. In the example of FIG. 1, system 10 includes main console 12, hand held remote control 14, syringe holder 16, syringe 18, syringe plunger 20, contrast medium reservoir (e.g., bottle) 22, inlet valve system 24, manifold 26, high pressure tube 28, catheter 30, patient medication port 32, three-way stop-cock 34, T-connector 36, pressure transducer 38, stop-cock 40, tubing 42, peristaltic pump 44, saline check valve 46, saline reservoir 50, and reservoir support rack 53. Contrast medium injection system 10 is only one example of a configuration of a powered injector that can be used in accordance with the disclosure. In other examples, contrast medium injector system 10 may include a second syringe holder, a second syringe main body, and a second syringe plunger in communication with a saline reservoir instead of the peristaltic pump shown in FIG. 1.

In the example of FIG. 1, console 12 houses the electrical controls for system 10, together with the motor(s) which drive plunger 20 and peristaltic pump 44. Console 12 includes a user interface 54 that provides control switches 56 and display 58 through which a user may enter control settings and monitor the operational state of system 10.

Remote control 14 can be connected to console 12 by cable 60 (although in other examples remote control 14 may be connected by a wireless connection such as an RF, infrared optic, or ultrasonic link). Remote control 14 is, in the example of FIG. 1, a hand-held control which includes reset and saline push button switches 62 and 64, respectively, and flow rate control lever or trigger 66. By squeezing trigger 66, the user can provide a command signal to console 12 to control the rate at which medial fluid is discharged from syringe 18 and injected into catheter 30. In other examples, system 10 does not include remote control 14. In these examples, a user may control the operation of system 10 directly via console 12.

Syringe holder 16 in the example of FIG. 1 projects from the left hand side of console 12. Syringe holder 16 is configured to receive and hold a removable syringe. Syringe holder 16 may be fabricated from clear material and may open to receive a syringe and close to hold the syringe within a bounded cavity. In system 10, syringe holder 16 includes a half cylindrical back shell 68, a half cylindrical front door 70 (which is shown in open position in FIG. 1), and reservoir holder 72. A user may open half cylindrical front door 70, insert a disposable syringe 18 so that the syringe is positioned against half cylindrical back shell 68, and then close half cylindrical front door 70 so that the syringe is secured within syringe holder 16.

Syringe 18 is inserted into syringe holder 16 and defines an open end 74 connected to console 12 and a closed end 74 opposite the open end. Closed end 74 of syringe 18 contains at least one port which, in the illustrated example, is shown as two ports: inlet port 78 and outlet port 80. Inlet port 78 is in fluid communication with contrast medium reservoir 22. Outlet port 80 is in fluid communication with high pressure tube 28 which, in turn, is in fluid communication with catheter 30. Syringe 18 may or may not be fabricated from a transparent or translucent material such as plastic or glass.

During operation, plunger 20 is configured to advance and retract axially along the length of syringe 18. For example, starting with plunger 20 positioned inside of syringe 18 and fluid communication with high pressure tube 28 closed, the piston may be retracted (e.g., by withdrawing the piston from left to right in FIG. 1) to draw contrast medium from contrast medium reservoir 22 into syringe 18 via inlet port 78. Thereafter, fluid communication between contrast medium reservoir 22 and syringe 18 via inlet port 78 may be closed and fluid communication between the syringe and high pressure tube 28 via outlet port 80 opened. Advancing plunger forward within syringe 18 may compress liquid fluid (e.g., contrast medium) within the syringe, causing the fluid to discharge under pressure from the syringe into catheter 30.

In FIG. 1, contrast medium reservoir 22 is connected to inlet port 78 through inlet valve system 24. During operation, contrast medium is drawn from reservoir 22 through inlet valve system 24 and inlet port 78 into the pumping chamber defined by syringe 18 and plunger 20. Inlet valve system 24 may be a one-way valve that permits air to flow from syringe 18 back into reservoir 22 but which will not permit contrast medium to flow from syringe 18 to reservoir 22 when fully closed.

Outlet port 80 of syringe 18 in FIG. 1 is connected to manifold 26. Manifold 26 may include a spring biased spool valve which normally connects a saline port 82 and patient port 84. When contrast medium is being injected, the pressure of the contrast medium may cause the spool valve to change states so that outlet port 80 is connected to patient port 84 (i.e., as opposed to saline port 82). Other types of valves besides spring biased spool valves that selectively communicate between the contrast medium and the saline can be used, and the disclosure is not limited in this respect.

High pressure tube 28 in system 10 is a flexible tube connecting patient port 84 to catheter 30. A three-way stop-cock 34 is located at the distal end of tube 28. A rotatable luer lock connector 86 is connected to stop-cock 34 and mates with luer connector 88 at the proximal end of catheter 30. A stopcock 34 either blocks flow between tube 28 and catheter 30, permits flow, or connects medication port 32 to catheter 30 (for use when medication is to be delivered through catheter 30 to the patient).

To enable a user to monitor the performance of contrast medium injection system 10 during an injection operation, the system may include a pressure sensor or other monitoring hardware. In the example of FIG. 1, system 10 includes pressure transducer 38 that is configured to monitor blood pressure of a patient. When catheter 30 is placed within a patient and injection of contrast medium is not taking place, pressure transducer 38 can monitor the patient's blood pressure through a column extending from the patient through catheter 30, tube 28, patient port 84, manifold 26, saline port 82, tubing 90, T-connector 36, and tubing 92. In the example shown, transducer 38 has an associated stop-cock 40 which allows transducer 38 to be exposed to atmospheric pressure during calibration and also allows for removal/expulsion of trapped air so the dome chamber of transducer 38 can be flushed with saline.

In some examples, system 10 also includes a pressure sensor (e.g., a pressure transducer) configured to measure a pressure of the contrast medium as the contrast medium is discharged from syringe 18. For example, system 10 may include a pressure transducer that is separate from pressure transducer 38 configured to measure a patient's blood pressure. The pressure transducer may measure a pressure of the contrast medium as the contrast medium is discharged from syringe 18 for developing simulated contrast medium formulations. When used, the pressure sensor may be in fluid communication with outlet port 80 and/or catheter 30 and configured to measure the pressure of the contrast medium during high pressure injection. In one example, the pressure sensor is configured to measure a pressure of a contrast medium (and/ or a simulated contrast medium) at a location between high pressure tube 28 and catheter 30. Data from the pressure sensor may indicate to a user the pressure at which contrast medium is forcibly injected into a patient during operation and/or the pressure at which a simulated contrast medium would be forcibly injected into a patient, were the simulated contrast medium being injected into a patient. As noted above through, a clinician would not actually inject the simulated contrast medium into a patient when testing hardware.

System 10 in the example of FIG. 1 also includes peristaltic pump 44. Peristaltic pump 44 supplies saline solution from reservoir 50 through saline check valve 46, tubing 42, T-connector 36 and tubing 90 to saline port 82. When peristaltic pump 44 is operating to supply saline solution, the saline solution may be supplied through manifold 26 to patient port 84 and then through tube 28 to catheter 30. In other examples, system 10 does not include peristaltic pump 44. Rather, in these examples, system 10 may include a second syringe and plunger assembly that is in selective fluid communication with catheter 30. The plunger may retract and advance within the second syringe to draw saline into the syringe and discharge the saline from the syringe into catheter 30, similar to the process described above with respect to syringe 18 and plunger 20.

In use, a user may enter into system 10 the safety parameters that will apply to the injection of radiographic contrast material. These safety parameters typically include the maximum amount of radiographic contrast material to be injected during any one injection, the maximum flow rate of the injection, the maximum pressure developed within syringe 18, and the maximum rise time or acceleration of the injection. To actuate an injection of contrast material, the user may operate remote control 14 by squeezing trigger 66. Within the preset safety parameters, system 10 causes the flow rate of the injection to increase as the force or distance of travel of trigger 66 is increased.

Figure 2:
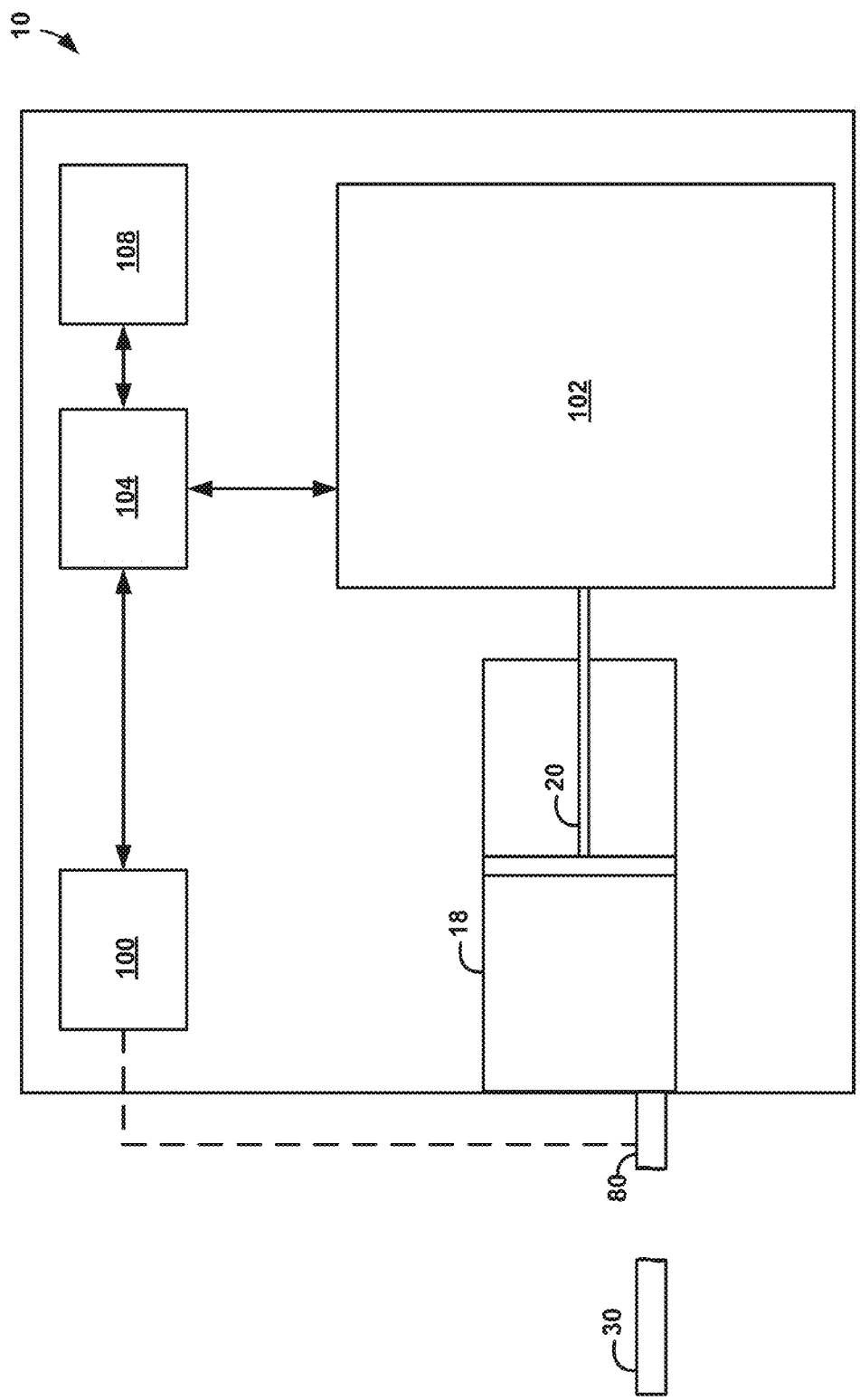
FIG. 2 is a functional block diagram illustrating example components of the medical fluid injection system of FIG. 1.

FIG. 2 is a functional block diagram illustrating components an example of contrast medium injection system 10, which includes syringe 18, plunger 20, catheter 30, and outlet port 80 previously described with respect to FIG. 1. Injection system 10 in the example of FIG. 2 also includes a pressure sensor 100, a motor 102, a processor 104, and a memory 108. Processor 104 is communicatively coupled to pressure sensor 100, motor 102, and memory 108. Pressure sensor 100 is configured to measure the pressure of contrast medium discharged from syringe 18 during high pressure injection, e.g., for developing simulated contrast media formulations. Motor 102 is configured to advance and retract plunger 20 within syringe 18, e.g., for filling the syringe with contrast medium and discharging the contrast medium form the syringe into catheter 30.

During operation of contrast injection system 10, processor 104 controls the filling and discharge of contrast medium from syringe 18 with the aid of instructions associated with program information stored in memory 108. Processor 104 may also control the filling and discharge of contrast medium from syringe 18 based on instructions received from a user, e.g., via main console 12 and/or hand held remote control 14 in FIG. 1. Instructions executed by processor 104 may, for example, define fluid delivery programs that specify the quantity, rate, and/or pressure with which contrast medium is to be delivered from syringe 18 into catheter 30 during a diagnostic imaging procedure and/or during operational testing of system 10. Instructions executed by processor 104 may also control the opening and closing of valves within system 10 to fill syringe 18 with contrast medium and to discharge the contrast medium from the syringe.

Processor 104 of contrast medium injection system 10 may each include one or more processors, such as one or more microprocessors, digital signal processors (DSPs), application specific integrated circuits (ASICs), field programmable gate arrays (FPGAs), programmable logic circuitry, or the like, either alone or in any suitable combination. In general, processor 104 may receive electrical signals from input devices such as remote control 14 and front panel controls 56 and provide electrical signals to output devices such as display 58 and motor 102. For example, processor 104 may provide signals to display 58 that cause the display to display operation data, alerts, status information, and operator prompts. As another example, processor 104 may provide signals to motor 102 to control the advancing and retracting motion of plunger 20 through a motor drive circuit.

Memory 108 may store instructions and related data that, when executed by processor 104, cause contrast injection system 10 and processor 104 to perform the functions attributed to them in this disclosure. For example, memory 108 of contrast injection system 10 may store instructions for execution by processor 104 including, e.g., commands for actuating valves, instructions for filling and/or discharging syringe 18, instructions for monitoring and comparing a signal generated by pressure sensor 100, and any other information regarding the system 10.

Contrast medium injection system 10 in the example of FIG. 2 also includes pressure sensor 100. Pressure sensor 100 is configured to measure a pressure of the contrast medium as the contrast medium is discharged from syringe 18. For example, pressure sensor 100 may measure a pressure of the contrast medium at the discharge end of syringe 18 so as to generate indicative of pressure of the discharged contrast medium versus time. The data may indicate how the discharge pressure of the contrast medium varies over time during an injection operation, e.g., as plunger 20 advances through syringe 18 (e.g., from right to left in the example of FIG. 2). Processor 104 may receive data from pressure sensor 100 and store the data in memory 108.

While pressure sensor 100 is shown in FIG. 2 as being contained within contrast medium injection system 10 and in direct communication with processor 104, it should be appreciated that the depiction of the pressure sensor in this configuration is for descriptive purposes only. The functionality of the hardware and software of contrast medium injection system 10, including pressure sensor 100, may be realized by separate hardware, firmware, or software components that, in combination, perform the functions attributed to the components in this disclosure. Further, in still other examples, contrast medium injection system 10 does not include pressure sensor 100. Instead, in these examples, contrast medium injection system 10 may determine a pressure of a contrast medium (or simulated contrast medium) during high pressure injection indirectly rather than through direct pressure measurement. For example, system 10 may measure the amount of current motor 102 requires to advance plunger 20 and determine, based on the measured current, the pressure of the contrast medium during injection. The more motor current, the higher the pressure.

In some examples, processor 104 or a processor of a different computing device may be configured to analyze a signal indicative of a contrast medium injection pressure such as a signal generated by pressure sensor 100. For example, as discussed in greater detail below, processor 104 or a processor of a different computing device may analyze a signal generated by pressure sensor 100 for generating a simulated contrast medium. The analysis may indicate to a user how the composition of the simulated contrast medium should be adjusted to better match the properties of an active contrast medium the simulated contrast medium is designed to simulate.

Contrast medium injection system 10 in the example of FIGS. 1 and 2 may perform a variety of operations under the control of processor 104. Example operations includes contrast fill, air purge, and inject operations. In different applications, system 10 can also be configured to perform many other types of operations including, for example, saline flush and patient pressure monitoring operations.

Figure 3:
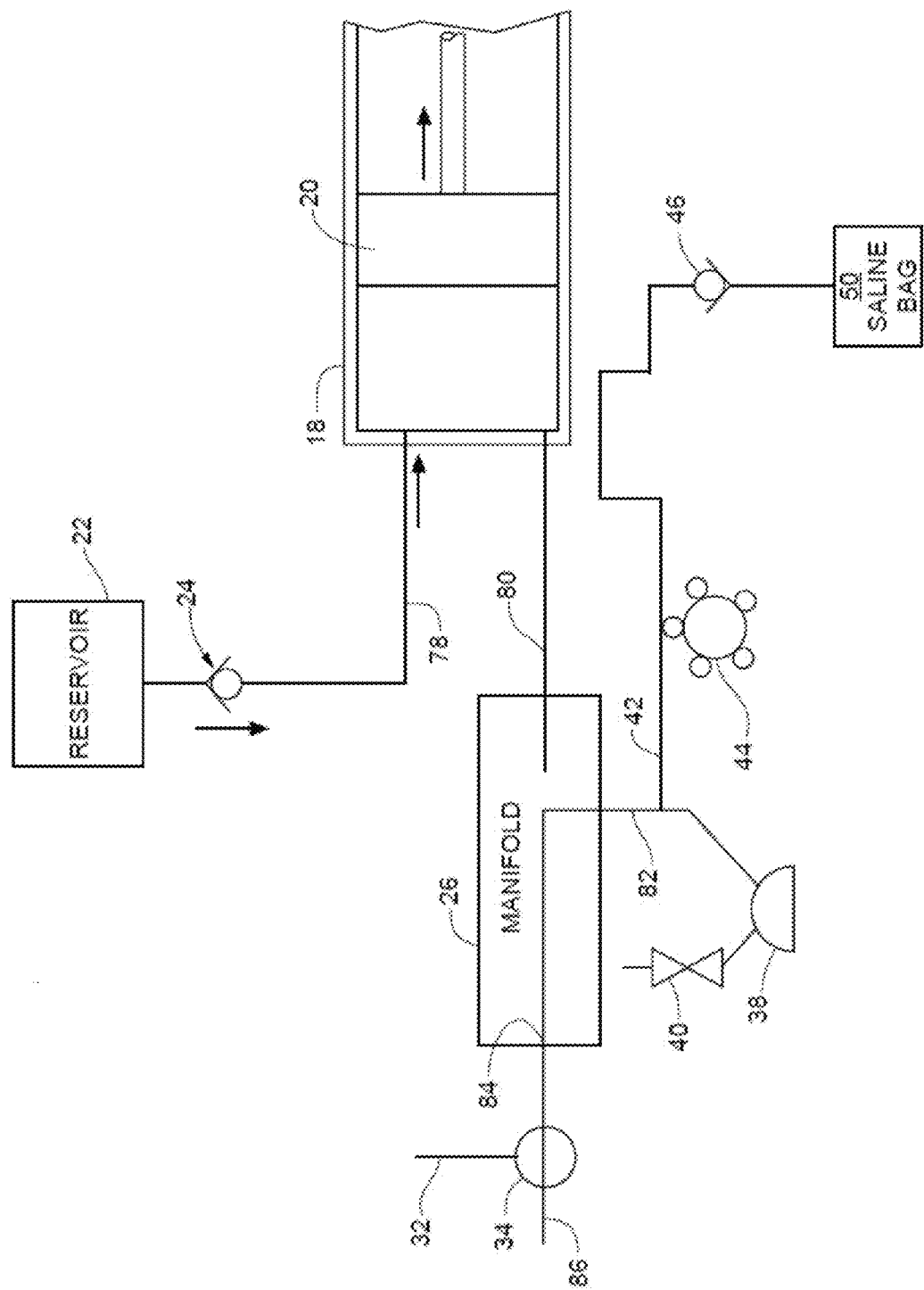
FIG. 3 is a block diagram showing an example contrast fill operation that may be performed using the system of FIGS. 1 and 2.

FIG. 3 is a block diagram showing an example contrast fill operation that may be performed using system 10. In response to control signals from processor 104, motor 102 (FIG. 2) may retract plunger 20 within syringe 18 to draw contrast media from reservoir 22 and fill the syringe. The contrast fill operation may be performed during initial set up of system 10, e.g., before a diagnostic imaging procedure, and/or before testing contrast medium injection system 10 to ensure that the system is working properly. During the filling operation, plunger 20 may initially be driven to its furthest forward position adjacent closed end 76 (FIG. 1) of syringe 18. This will expel to the atmosphere the majority of the air which is located within syringe 18. Plunger 20 is then refracted within syringe 18, creating a vacuum within the syringe that draws contrast from reservoir 22 through inlet valve system 24 and into syringe 18 via inlet port 78.

Figure 4:
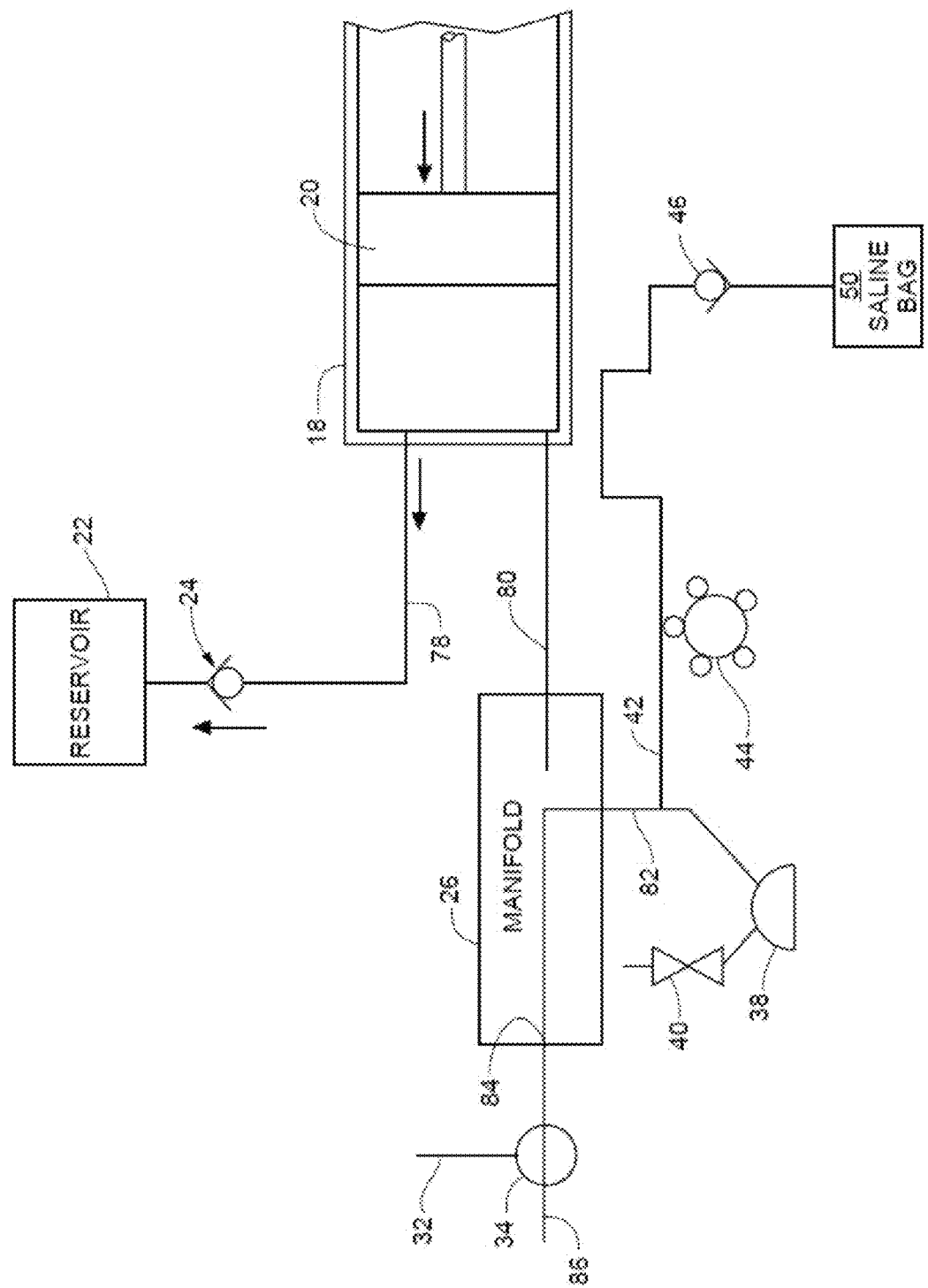
FIG. 4 is a block diagram showing an example air purge operation that may be performed using the system of FIGS. 1 and 2.

In some examples, the contrast fill operation results in some air being drawn into or remaining within syringe 18. To prevent air within syringe 18 from being injected into a patient through catheter 30 during a patient injection operation, the air may be purged from the syringe prior to injecting contrast medium into the patent. FIG. 4 is a block diagram showing an example air purge operation that may be performed using system 10.

During an air purge operation as illustrated in FIG. 4, processor 104 controls motor 102 to advance plunger 20 forward, expelling trapped air from within syringe 18. The air, being lighter than the contrast medium, may collect near the top of syringe 18 adjacent outlet port 80. As plunger 20 moves forward, the air can be expelled from syringe 18 through inlet port 78 and inlet valve system 24. In some examples, inlet valve system 24 allows flow of contrast media from reservoir 22 to inlet port 78, but will not allow contrast media to flow in the opposite direction from inlet port 78 to reservoir 22. Inlet valve system 24 may, however, allow air to flow from port 78 to reservoir 22 until sufficient pressure builds in the syringe to close the inlet valve system.

Figure 5:
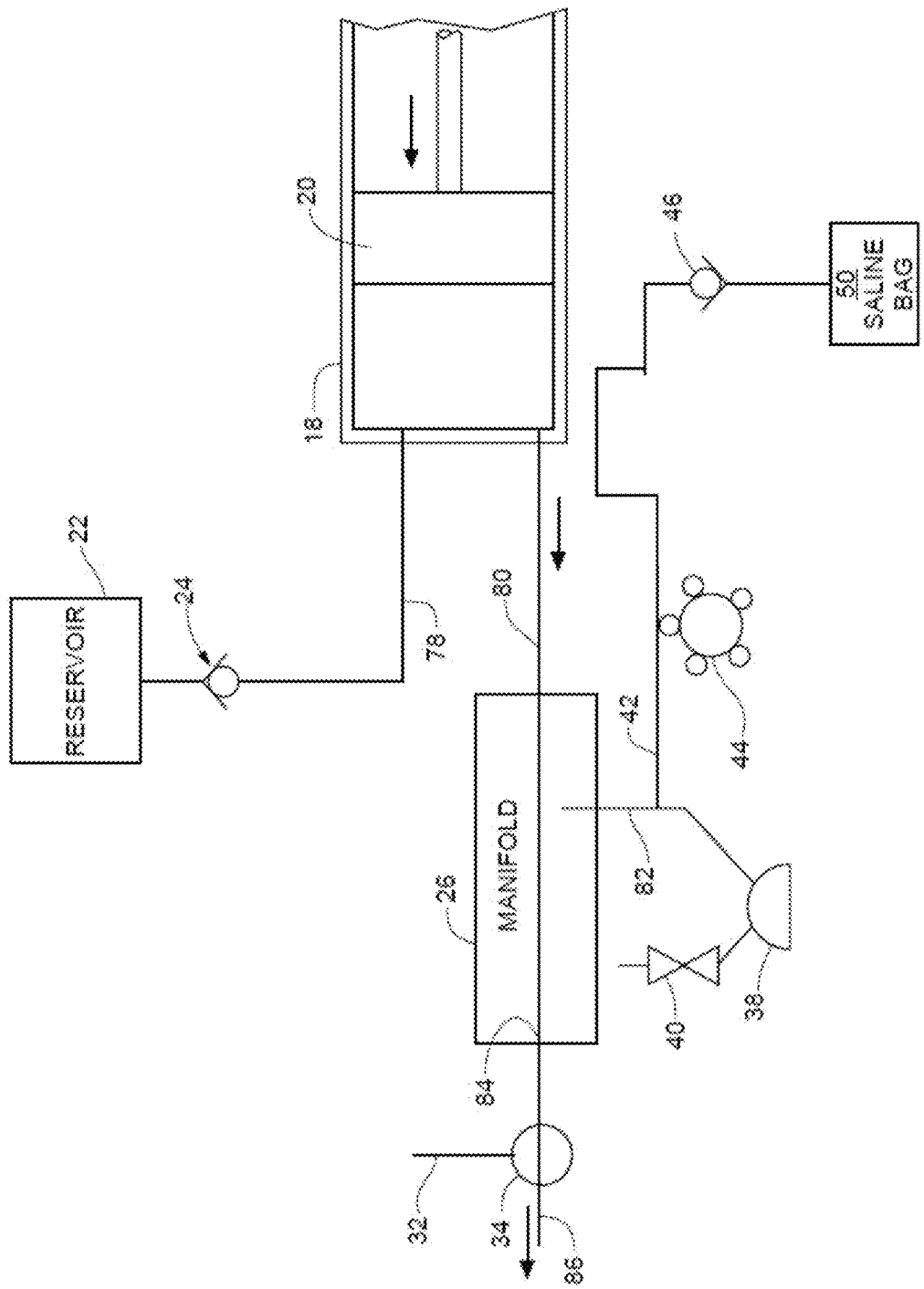
FIG. 5 is a block diagram showing an example contrast injection operation that may be performed using the system of FIGS. 1 and 2.

FIG. 5 is a block diagram showing an example contrast injection operation that may be performed using system 10. As shown in this example, processor 104 controls motor 102 to advance plunger 20 forward, creating hydraulic pressure to force contrast material out of syringe 18 through outlet port 80 and through manifold 26 and high pressure tube 28 into catheter 30. In some examples, processor 104 controls motor 102 in response to commands received from a user, e.g., via main console 12 and/or hand held remote control 14. The commands may dictate the rate and/or volume of contrast medium to be discharged from syringe 18 and injected out of outlet port 80. In some examples, as shown in FIG. 5, syringe outlet port 80 and patient port 84 are connected for fluid flow during the patient inject operation.

When configured with manifold 26, the manifold may contain a valve that controls the routing of fluid connections between patient port 84 and either syringe outlet port 80 or saline port 82. In some examples, manifold 26 includes a spool valve which is spring biased so that patient port 84 is normally connected to saline port 82. When the pressure at syringe outlet port 80 builds with the movement of plunger 20 forward, the bias force against the spool valve is overcome so that syringe outlet port 80 is connected to patient port 84, and saline port 82 is disconnected from the valve within manifold 26. The spool valve may open automatically during the patient inject operation in response to increase pressure exerted on it from the syringe outlet port 80. In addition, the spool valve may close and return to its original position allowing for connection of patient port 84 to transducer 38 when a slight vacuum is applied by retraction of plunger 20 at the end of each patient inject operation. In other examples, the valve within manifold 26 may be an electromechanical or motor driven valve that is actuated at appropriate times to connect either syringe outlet port 80 or saline port 82 to patient port 84. In such examples, the actuator mechanism can be controlled by console 12.

When injecting a contrast medium that contains an active contrast agent into a patient, patient port 84 may be connected to (e.g., in fluid communication with) a catheter that is inserted into the patient. This will deliver the contrast medium from the injector to the patient. By contrast, when injecting a simulated contrast medium that does not include an active contrast agent, patient port 84 may be in fluid communication with a waste reservoir (e.g., a waste receptacle, a drain). This will allow the simulated contrast medium to be disposed of after passing through the injector.

During operation of contrast medium injection system 10, syringe 18 may be filled with any suitable type of contrast medium and then discharged to inject pressurized contrast medium through outlet port 80. The type of contrast medium used for a particular application may depend on a variety of factors such as, e.g., the physiological condition of the patient and the type of diagnostic imaging procedure the patient is undergoing. In general, when injected during a diagnostic imaging procedure, the contrast medium contains an active contrast agent that interacts with radiation or electromagnetic energy from a diagnostic imaging machine to enhance the visual contrast of structures or fluids within a body of the patient, e.g., as compared to structures or fluids not exposed to the contrast agent.

In some examples, the active contrast agent is a radiopaque agent that is opaque to x-rays or similar radiation. For example, the active contrast agent may be an organically (i.e., non-ionic) or non-organically (i.e., ionic) bound molecule, such as organically or non-organically bound iodine. Example iodine-based contrast media include diatrizoate (Hypaque™ 50), metrizoate (Isopaque 370), ioxaglate (Hexabrix), iopamidol (Isovue® 370), iohexol (Omnipaque™ 350), ioxilan (Oxilan® 350), iopromide (Ultravist® 370), and iodixanol (Visipaque™ 320). Other example radiopaque agents include barium-based agents such as barium sulfate. In still other examples, the active contrast agent may be a radioisotope that can be detected during nuclear magnetic resonance imaging or a positron emitting isotope that can be detected during positron emission tomography. The type of contrast medium used in system 10 can be established by placing a selected type of contrast medium in reservoir 22 (FIG. 1) for injection via syringe 18.

To ensure that contrast medium injection system 10 is operating properly prior to being placed in service and, in some applications, even after being placed in service, the injector may be tested by filling reservoir 22 with contrast medium and then operating the injector to discharge the contrast medium from the injector. Unlike injection during a diagnostic imaging procedure, however, the contrast medium is not discharged from the injector into a patient. Instead, the contrast medium is discharged from the injector into a waste receptacle. The test injection may be used to confirm that various components of the injector such as a motor and gears are operating properly and that the fluid connections in the injector provide fluid integrity of the system.

While contrast medium with an active contrast agent can be used to test the performance of an injector outside of a medical procedure, use of the contrast medium may expose test personnel to the active agent and create waste that is difficult to dispose. For these and other reasons, contrast medium injection system 10 may, in accordance with some examples, operate using a simulated contrast medium rather than a contrast medium with an active contrast agent. The simulated contrast medium may simulate the behavior of the contrast medium, e.g., during the filling of syringe 18 and discharge from the syringe, but may lack an active contrast agent that provides visual contrast in a diagnostic imaging procedure.

When the simulated contrast medium replicates the behavior of the active contrast medium in the injector, an operator can use the simulated contrast medium to accurately evaluate the operational performance of system 10 without having the handling and disposal risks associated with the active contrast medium. For example, an operator can load the simulated contrast medium into reservoir 22 and engage contrast medium injection system 10 to perform one or more syringe fill and discharge procedures. During the syringe fill and discharge procedures, the operator may monitor various fluid connections and hardware (e.g., motor 102 and gears) in system 10 to detect any issues that may warrant attention before placing the system in service. In this way, the simulated contrast medium can be used to evaluate the operational integrity of contrast medium injection system 10 without having the risks attendant to working with active contrast media.

Depending on the configuration of the simulated contrast medium, the simulated contrast medium may be devoid of any active contrast agents that provide contrast during diagnostic imaging. For example, the simulated contrast medium may not have any atoms or molecules that function to provide contrast during imaging added to the medium. In the example of a contrast medium that includes an iodine-base active contrast agent, for instance, the simulated contrast medium may be devoid of iodine. In some examples, the simulated contrast medium is devoid of the atoms or molecules that function to provide contrast during imaging by having less than 0.1 wt % of the atoms or molecules such as, e.g., less than 0.01 wt %, or zero weight percent. In some examples, the concentration of an atom or molecule in a simulated contrast medium that functions to provide contrast during imaging may be such that, were the simulated contrast medium injected into a patient, the simulated contrast medium would not cause a contrast between structures or fluids infused with the simulated contrast medium and adjacent structures or fluids not infused with the simulated contrast medium. For example, the atom or molecule in the simulated contrast medium may not cause contrast during a diagnostic imaging procedure including, but not limited to, X-ray, computed tomography (CT), nuclear magnetic resonance (NMR)/magnetic resonance (MR), ultrasound, fluoroscopy, and positron emission tomography (PET). Were the simulated contrast medium to be exposed to radiation or electromagnetic energy from a diagnostic imaging machine, the simulated contrast medium may be transparent to the radiation or electromagnetic energy so that the simulated contrast medium does not provide contrast.

The specific composition and characteristics of a simulated contrast medium suitable for use in contrast medium injection system 10 may vary, e.g., based on the type of active contrast media intended to be used in the system during medical procedures. In some examples, the simulated contrast medium is configured to exhibit at least one (and, optionally, multiple) flow property equal or substantially equal to that of an active contrast medium intended to be injected during a diagnostic procedure using injection system 10. Example flow properties include, but are not limited to, viscosity, surface tension, pressure of the fluid during injection (e.g., a maximum pressure during injection), and density. In some additional examples, the simulated contrast medium is configured to exhibit at least one (and, optionally, multiple) other property equal or substantially equal to that of an active contrast medium intended to be injected during a diagnostic procedure using injection system 10, such as electrical conductivity and/or thermal conductivity. A property of a simulated contrast medium may be equal or substantially equal to a property of a contrast medium with an active contrast agent in that the property of the simulated contrast medium may be equal or substantially equal to the corresponding property of the active contrast medium. For example, depending on the application, a property of a simulated contrast medium may be within a range of plus or minus 25% of a corresponding value of an active contrast medium such as, e.g., with a range of plus or minus 15% of a corresponding value, a range of plus or minus 5% of a corresponding value, or a range of plus or minus 1% of a corresponding value.

By configuring a simulated contrast medium so that it exhibits a flow property equal or substantially equal to that of an active contrast medium, the simulated contrast medium may imitate the flow behavior and injection characteristic of the active contrast medium during operation of system 10. Accordingly, the simulated contrast medium can be used to reliably test and validate the operational integrity of an injection system and/or related hardware such as a patient disposable tubing kit. If the simulated contrast medium does not exhibit a flow property equal or substantially equal to that of the active contrast medium, contrast injection system 10 may behave differently during the filling of syringe 18 and injection of the simulated contrast medium, e.g., into catheter 30. For example, the simulated contrast medium may not provide the same back pressure when being pushed through outlet port 80 and catheter 30 by plunger 20 as compared to when syringe 18 is filled with an active contrast medium. In turn, operation of injection system 10 with the simulated contrast medium in this example may not accurately indicate to an operator how the system will behave in subsequent use with an active contrast agent.

A simulated contrast medium configured to be used in contrast medium injection system 10 can be formed of any suitable chemical components. In general, the specific chemical components used in the medium will be selected so that the simulated contrast medium exhibits a flow property equal or substantially equal to that of an active contrast medium intended to be used in system 10. In some examples, the simulated contrast medium includes a diluent and a simulated contrast agent. The diluent may be a bulk liquid component that forms a majority of the weight of the simulated contrast agent. The simulated contrast agent may be a component that does not provide contrast during an imaging procedure but rather modifies a flow property of the simulated contrast medium so that the flow property is equal or substantially equal to that of an active contrast medium. Depending on the application, the simulated contrast agent may also be referred to as a property modifier (e.g., a flow property modifier).

In one example, the simulated contrast medium includes water as a diluent and an organic polymer as a simulated contrast agent. The organic polymer may be added to the water to a weight percentage sufficient to cause the simulated contrast medium to exhibit a flow property (e.g., viscosity)

equal or substantially equal to that of a contrast medium that contains an active contrast agent. Example organic polymers that may be used in the simulated contrast medium include, but are not limited to, polyvinyl alcohol, polyethylene glycol, and starch. In different examples, the organic polymer may range from approximately 0.1 wt % to approximately 10 wt % of the simulated contrast medium such as, e.g., from approximately 1 wt % to approximately 5 wt % of the simulated contrast medium.

In some examples, the simulated contrast medium includes (or, optionally, consists or consists essentially of) polyvinyl alcohol and water. The polyvinyl alcohol may range from approximately 0.1 wt % to approximately 10 wt % of the simulated contrast medium such as, e.g., from approximately 1 wt % to approximately 5 wt % of the simulated contrast medium. An example polyvinyl alcohol that may be suitable for use in the simulated contrast medium is a polyvinyl alcohol manufactured under the tradename Elvanol 71-30 by DuPont®.

In general, contrast media that contain active contrast agents exhibit viscosities greater than that of water. Accordingly, in applications in which a simulated contrast medium is formulated to exhibit a viscosity equal or substantially equal to that of a contrast medium that contains an active contrast agent, the simulated contrast medium may also exhibit a viscosity greater than that of water. In different examples, the simulated contrast medium may exhibit a viscosity greater than 1 centipoise (cp) such as, e.g., a viscosity greater than approximately 1.5 cp. In some examples, the simulated contrast medium exhibits a viscosity range from approximately 1 cp to approximately 50 cp such as, e.g., a viscosity ranging from approximately 1.5 cp to approximately 25 cp. The foregoing viscosity values are merely examples, however, and it should be appreciated that a simulated contrast medium in accordance with the disclosure is not limited in this respect.

As examples, some commercially available contrast media exhibit the following viscosities: IOMERON 150 (viscosity of 1.4 cP at 37 degrees Celsius), RENO-60 (viscosity of 4.0 cP), ISOVUE-370 (viscosity of 20.29 cP), and IOMERON-400 (viscosity of 27.5 cP). Therefore, in instances in which a simulated contrast medium is formulated to exhibit a viscosity equal or substantially equal to one or more of the foregoing active contrast media, the simulated contrast medium may exhibit a viscosity equal or substantially equal to any one or more of the foregoing active contrast media.

In different examples, a contrast medium with an active contrast agent may behave as an isotropic Newtonian fluid or a thixotropic Non-Newtonian fluid. In an isotropic Newtonian fluid, the viscosity of the fluid is relatively constant as the fluid undergoes time-dependent shear stress. On the other hand, thixotropic Non-Newtonian fluid typically exhibit time-dependent changes in viscosity, where the longer the fluid undergoes shear stress, the lower its viscosity. This effect is sometimes referred to as shear thinning.

In instances in which a simulated contrast medium is intended to simulate an active contrast medium that behaves as a thixotropic fluid, the simulated contrast medium may also exhibit thixotropic behavior. By configuring the simulated contrast medium so that it exhibits the same or similar viscosity behavior as the active contrast medium, the simulated contrast medium may better imitate the filling and discharge behavior of the active contrast medium during operational testing.

Figure 6:
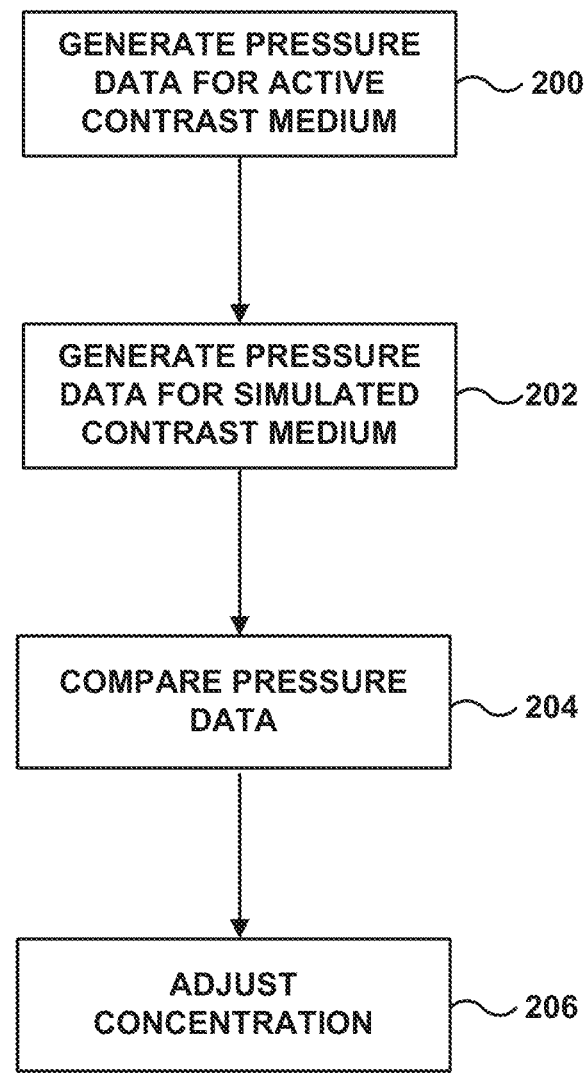
FIG. 6 is a flow diagram of an example technique for preparing a simulated contrast medium.
Figure 7A:
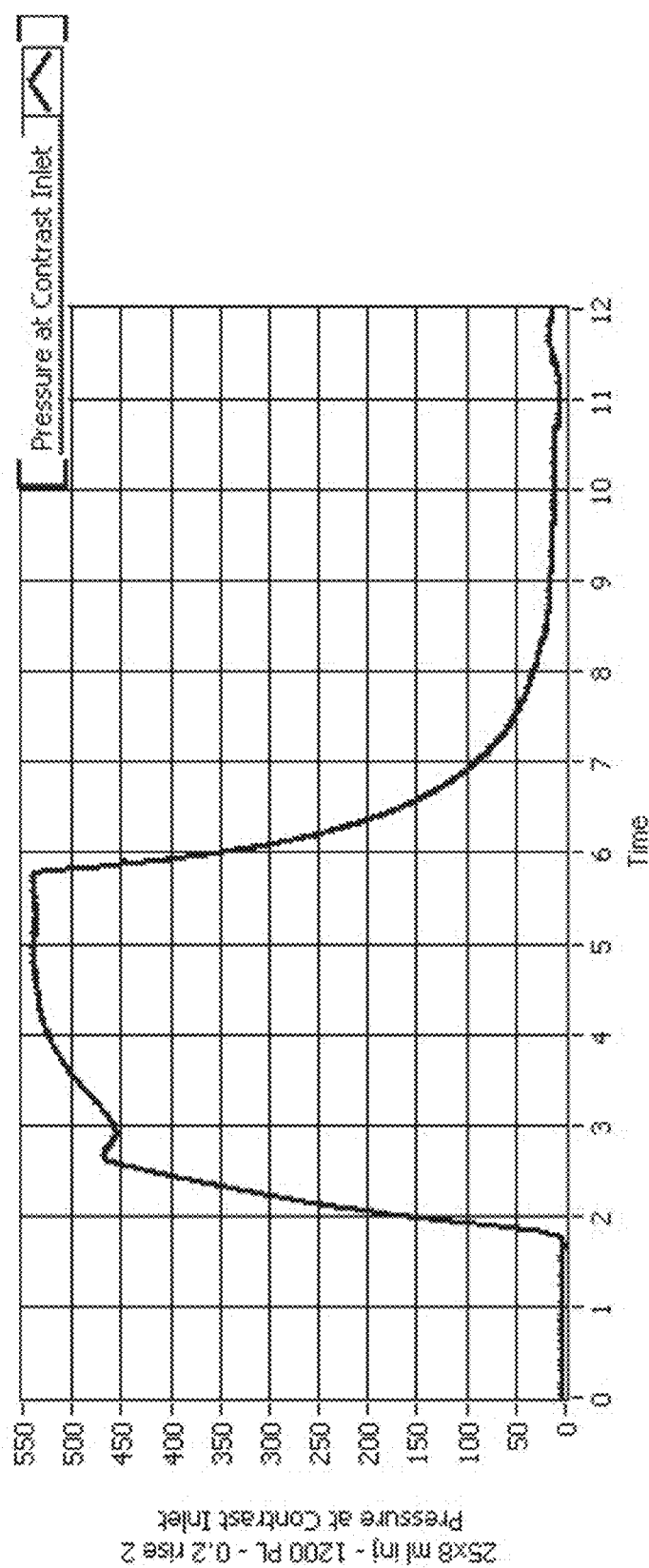
FIGS. 7A-7C are pressure versus time profiles for an example contrast medium containing an active contrast agent.
Figure 7B:
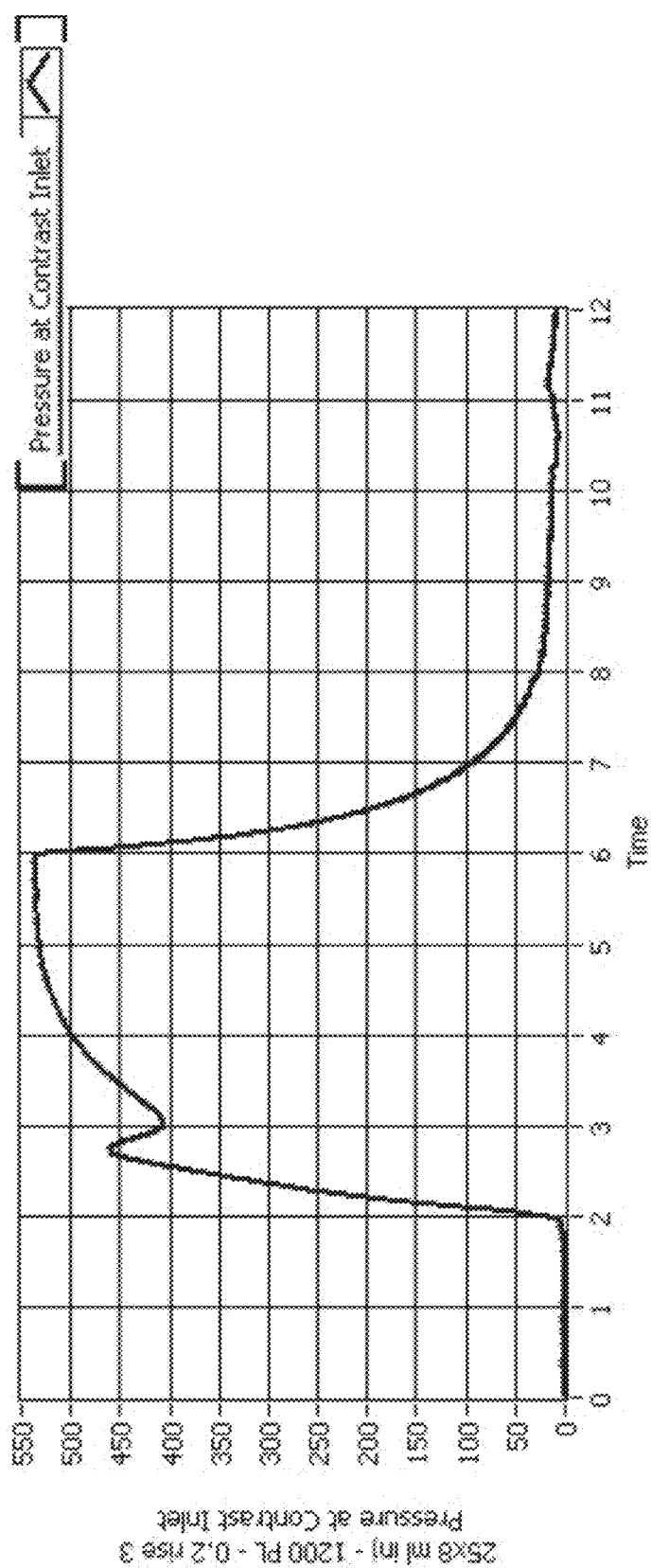
Figure 7C:
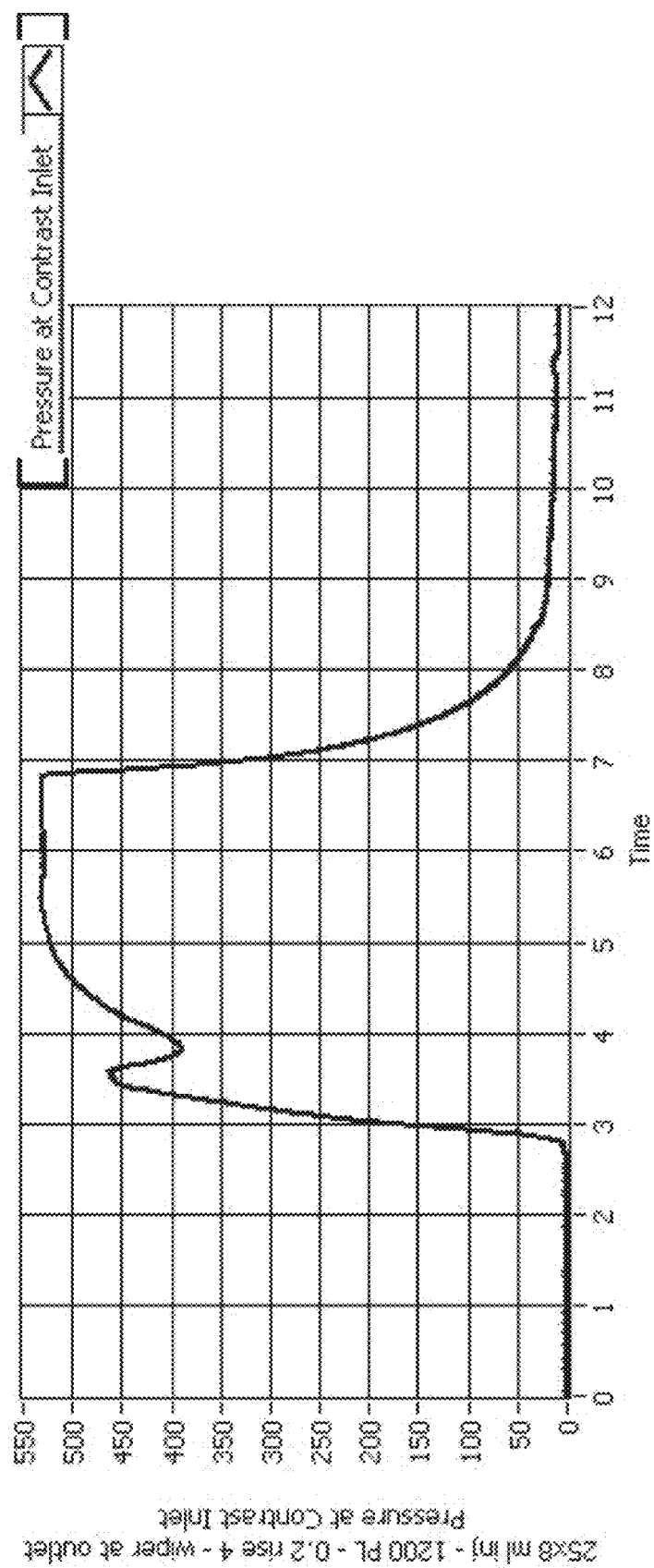
Figure 8A:
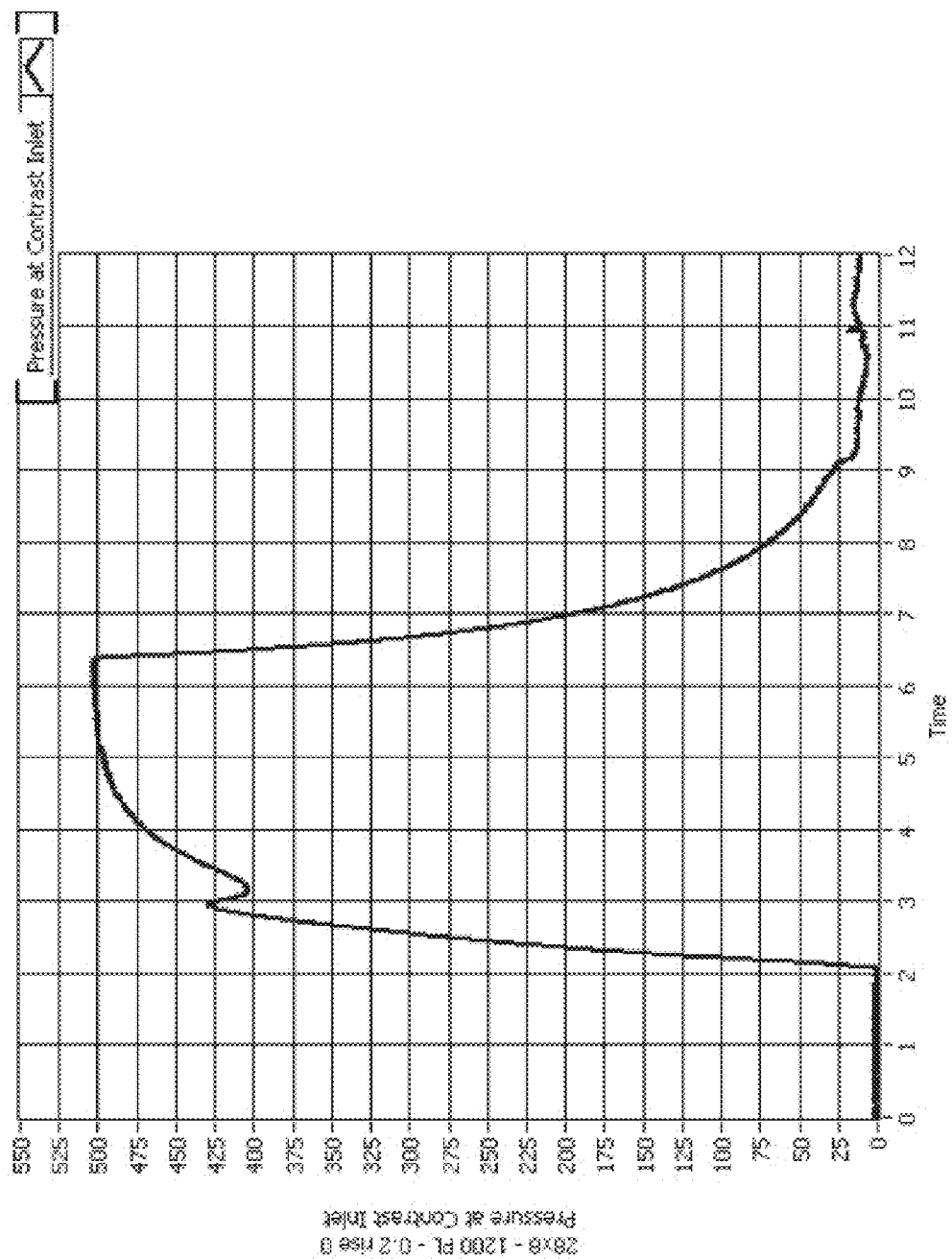
FIGS. 8A-8C are pressure versus time profiles for an example simulated contrast medium having a first concentration of a simulated contrast agent.
Figure 8B:
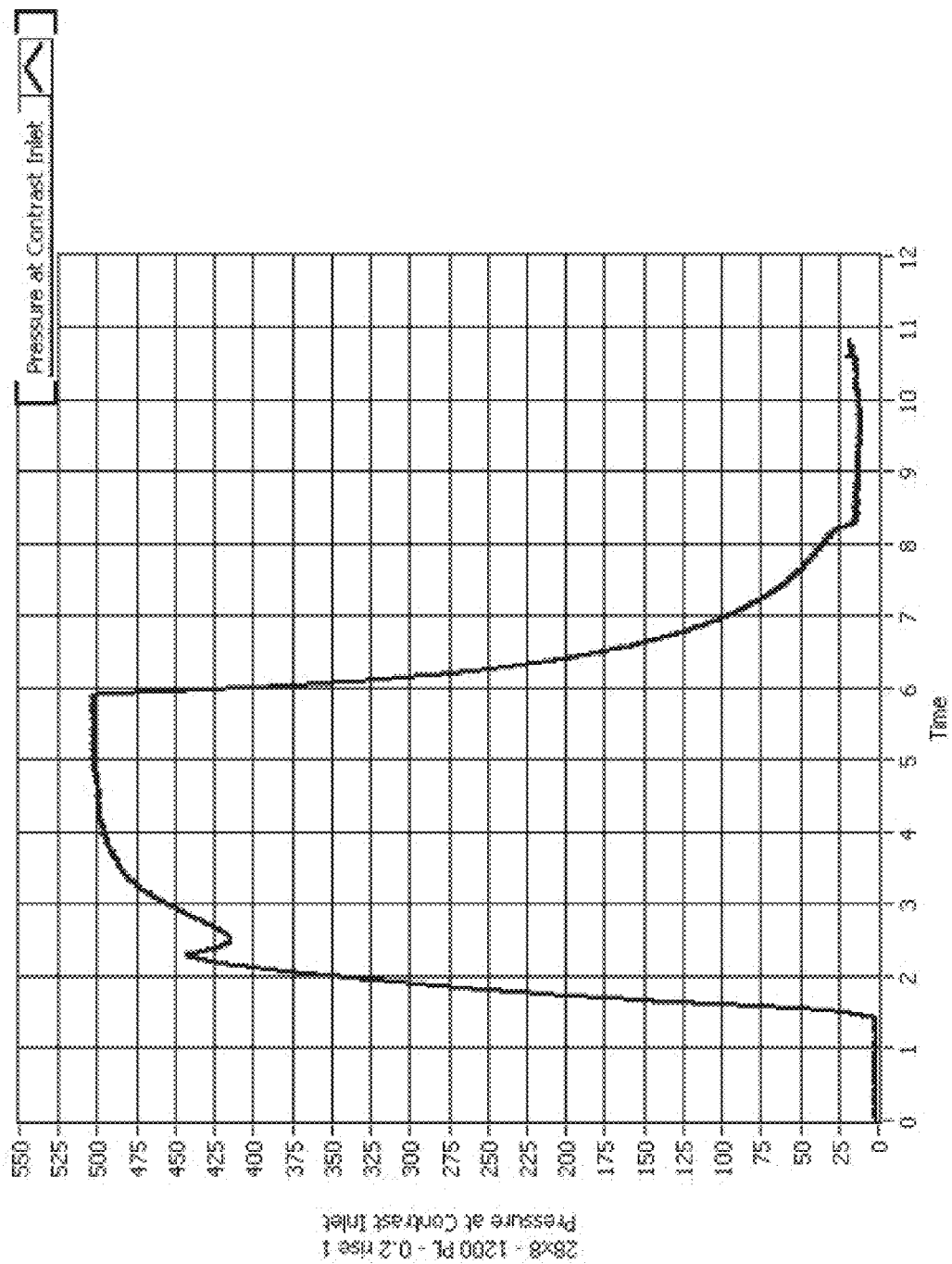
Figure 8C:
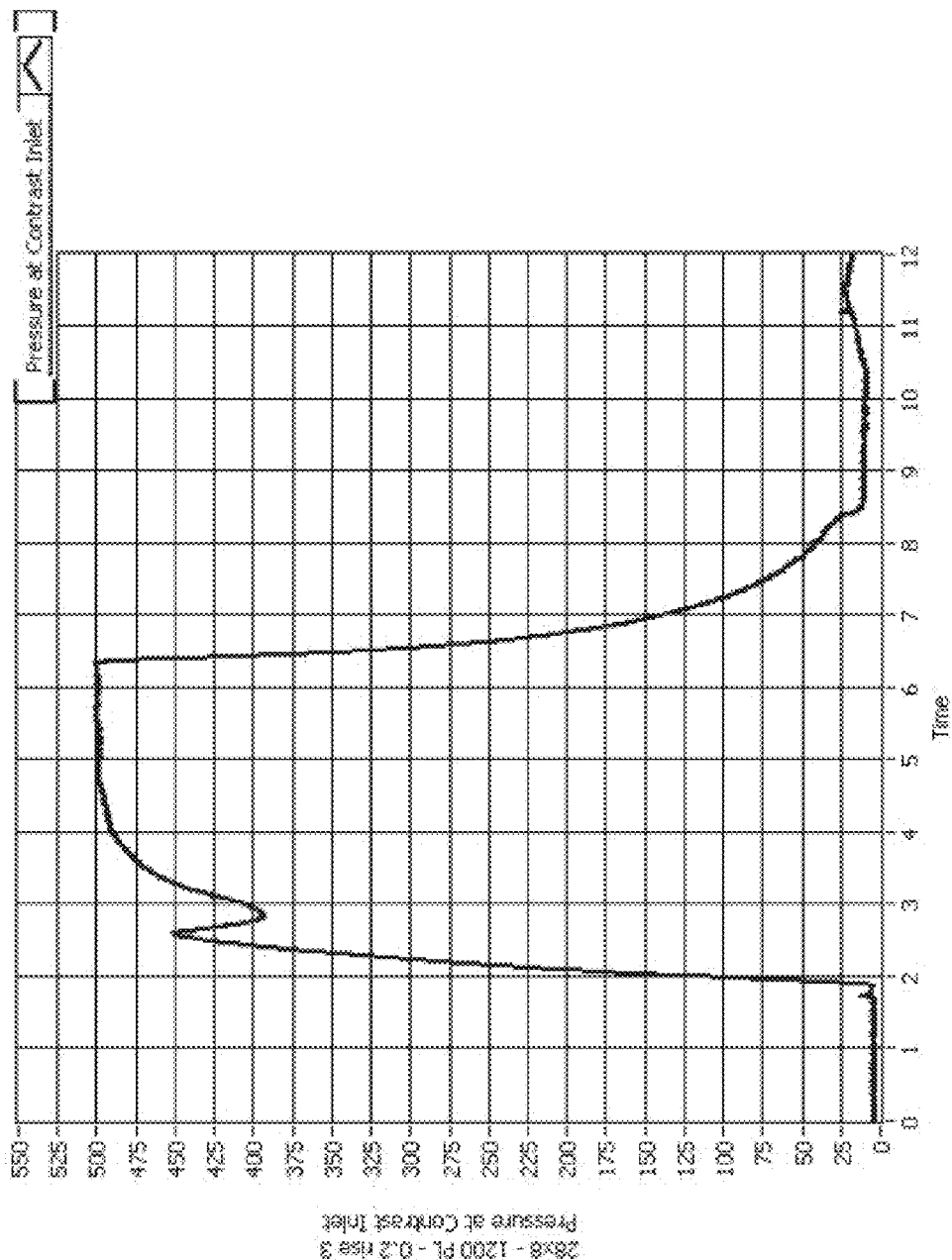
Figure 9A:
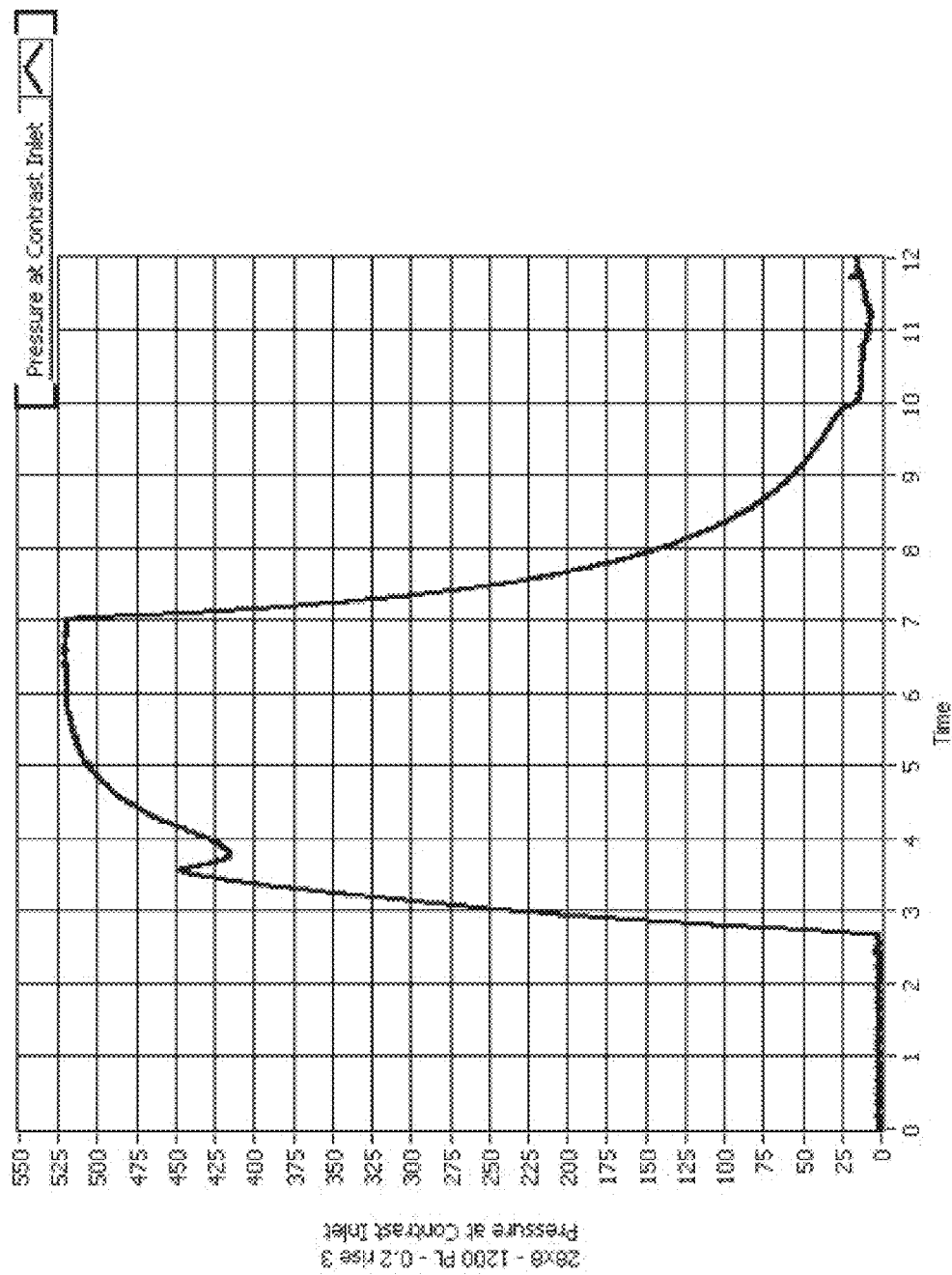
FIGS. 9A-9C are pressure versus time profiles for an example simulated contrast medium having a second concentration of a simulated contrast agent.
Figure 9B:
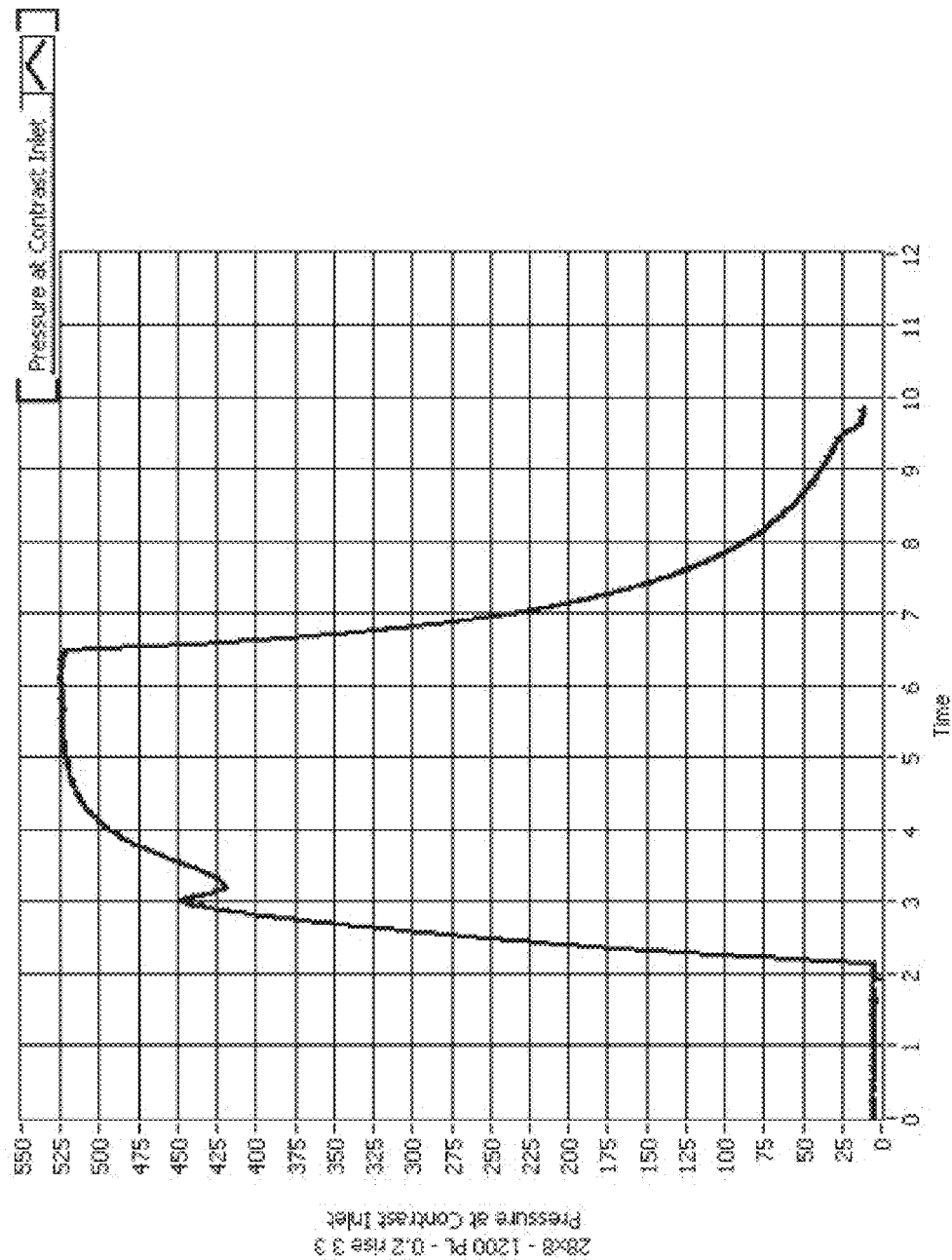
Figure 9C:
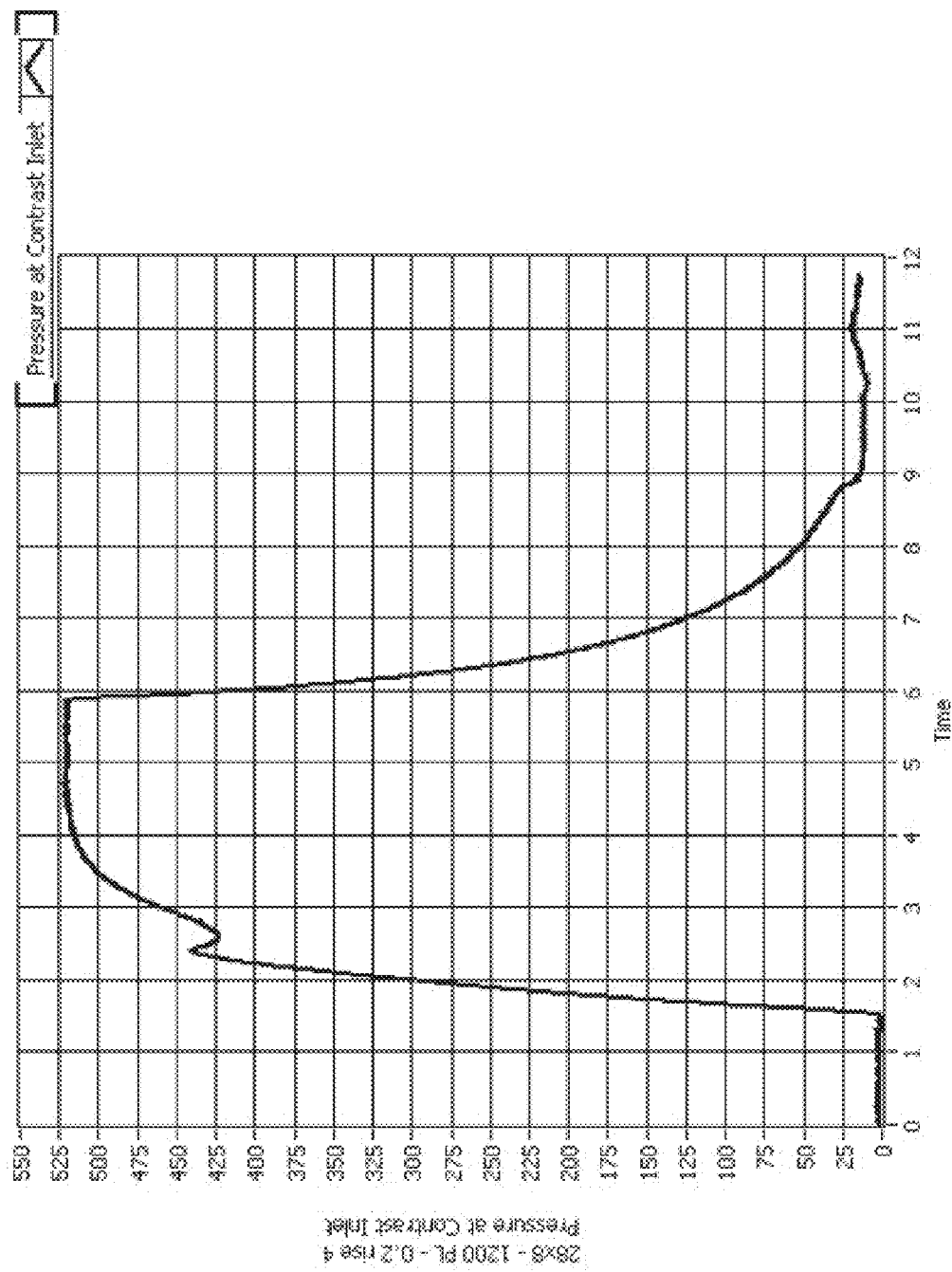

A variety of different contrast injection system configurations and contrast media have been described with respect to FIGS. 1-5. FIG. 6 is a flow diagram of an example technique for preparing a simulated contrast medium. For ease of description, the technique of FIG. 6 will be described with reference to contrast injection system 10 and processor 104 (FIGS. 1 and 2). Further, the technique of FIG. 6 will be described with reference to an example simulated contrast medium that includes polyvinyl alcohol and is designed to simulate an active contrast medium that includes organically bound iodine. It should be appreciated that technique of FIG. 6 may be performed using different contrast injection systems and computing devices as described herein. In addition, it should be appreciated that the techniques of FIG. 6 may use a simulated contrast medium having a different composition and/or is designed to simulate an active contrast medium having a different active contrast agent. The disclosure is not limited in these respects.

In the example of FIG. 6, pressure data is generated by injecting a contrast medium containing organically bound iodine through outlet port 80 from syringe 18 (200). Syringe 18 is filled with the organically bound iodine contrast medium from reservoir 22 during a fill operation. Subsequently, processor 104 controls motor 102 to advance plunger 20 into syringe 18 and discharge the contrast medium through outlet port 80 and, in some examples, into catheter 30. Pressure sensor 100 may measure the pressure of the contrast medium as the medium is ejected from the syringe so as to generate data indicative of how the discharge pressure of the contrast medium varies over time during the injection. For example, the data may indicate the pressure at outlet port 80 from an initial time when plunger 20 starts to advance within syringe 18 to a final time when the plunger stops advancing within the syringe. Depending on the configuration of injection system 10, a maximum pressuring during an injection operation may be greater than 400 pounds per square inch (psi) such as greater than 500 psi, greater than 800 psi, or even greater than 1000 psi. Processor 104 may receive the data from pressure sensor 100 and store the data as active contrast medium pressure data in memory 108.

Subsequent to generating pressure data from the contrast medium containing organically bound iodine, pressure data is generated from a simulated contrast medium that includes water as a diluent and polyvinyl alcohol as a simulated contrast agent (202). Syringe 18 is filled with the simulated contrast medium from reservoir 22 during a fill operation. Reservoir 22 initially filled with active contrast medium may be replaced with a reservoir filled with the simulated contrast medium prior to filling syringe 18. Subsequently, processor 104 controls motor 102 to advance plunger 20 into syringe 18 and discharge the simulated contrast medium through outlet port 80 and, in some examples, into catheter 30. Pressure sensor 100 may measure the pressure of the simulated contrast medium as the medium is ejected from the syringe so as to generate data indicative of how the discharge pressure of the simulated contrast medium varies over time during the injection. For example, the data may indicate the pressure at outlet port 80 from an initial time when plunger 20 starts to advance within syringe 18 to a final time when the plunger stops advancing within the syringe. Processor 104 may receive the data from pressure sensor 100 and store the data as simulated contrast medium pressure data in memory 108.

The technique of FIG. 6 also includes comparing the active contrast medium pressure data to the simulated contrast medium pressure data (204). For example, processor 104 may reference memory 108 and compare the active contrast medium pressure data to the simulated contrast medium pressure data. In some examples, an average pressure (e.g., mean pressure, median pressure) of the active contrast medium during injection is compared to an average pressure of the simulated contrast medium during injection. In other examples, a maximum or minimum pressure of the active contrast medium during injection is compared to a maximum or minimum pressure of the simulated contrast medium during injection. In still other examples, a pressure of the active contrast medium at a particular time in the injection process is compared to a pressure of the simulated contrast medium at the same particular time in the injection process. The active contrast medium pressure data may be compared to the simulated contrast medium pressure data, for example, by determine a difference between a pressure of the active contrast medium and a corresponding pressure of the simulated contrast medium.

Based on the comparison between the active contrast medium pressure data to the simulated contrast medium pressure data, a concentration of the polyvinyl alcohol in the simulated contrast medium may be adjusted (206). In different examples, the concentration of the polyvinyl alcohol may be increased by adding more polyvinyl alcohol to the simulated contrast medium or decreased by adding more water to the simulated contrast medium. The concentration of the polyvinyl alcohol may be adjusted to increase or decrease a flow property of the simulated contrast medium so that flow property is equal or substantially equal to a corresponding flow property of the active contrast medium. In some examples, the concentration of the polyvinyl alcohol is adjusted until a profile of pressure versus time as measure during injection for the simulated contrast media is substantially the same as a profile of pressure versus time as measured during injection for the active contrast media. By adjusting the concentration of the polyvinyl alcohol in the simulated contrast medium based on the comparison between the active contrast medium pressure data and the simulated contrast medium pressure data, the simulated contrast medium may be formulated to replicate the flow behavior of the active contrast medium.

The following non-limiting example may provide additional details about simulated contrast media in accordance with this disclosure.

Example

Pressure data was generated by injecting 25 milliliters (ml) of Isovue®-370, a contrast medium containing an organically bound iodine active contrast agent, at a rate of 8 ml/sec. The injection procedure was repeated three times to generate three pressure versus time profiles. The pressure data used to generate the profiles were measured during injection of the contrast medium. The three example pressure versus time profiles are provided as FIGS. 7A-7C. The average maximum pressure for the three injections was 536 psi.

Next, pressure data was generated by injecting 25 milliliters (ml) of a simulated contrast medium at a rate of 8 ml/sec. The simulated contrast medium included 3.3 wt % polyvinyl alcohol and a balance weight percentage water. Injection of the simulated contrast medium was repeated three times to generate three pressure versus time profiles. The pressure data used to generate the profiles were measured during injection of the simulated contrast medium. The three example pressure versus time profiles for the simulated contrast medium are provided as FIGS. 8A-8C. The average maximum pressure for the three injections was 504 psi.

Comparison of the average maximum peak pressure of the contrast medium to the average maximum peak pressure of the simulated contrast medium revealed that the pressures differed by 32 psi. In this example, the design target for the simulated contrast medium was to have average maximum peak pressure of the simulated contrast medium be within a range of plus or minus 25 psi of the average maximum peak pressure of the contrast medium. Accordingly, the concentration of polyvinyl alcohol in the simulated contrast medium was increased based on the comparison until the simulated contrast medium included 3.8 wt % polyvinyl alcohol and a balance weight percentage water.

Pressure data was generated by injecting 25 milliliters (ml) of a adjusted simulated contrast medium at a rate of 8 ml/sec. Injection of the simulated contrast medium was repeated three times to generate three pressure versus time profiles. The pressure data used to generate the profiles were measured during injection of the adjusted simulated contrast medium. The three example pressure versus time profiles for the adjusted simulated contrast medium are provided as FIGS. 9A-9C. The average maximum pressure for the three injections was 534 psi. Based on the design parameters set forth for the particular simulated contrast medium in this example, the simulated contrast medium exhibited a flow property substantially equal to a corresponding flow property of the contrast medium with the active contrast agent.

Various examples have been described. These and other examples are within the scope of the following claims.

The invention claimed is:

1. A method comprising:
   injecting, under the control of one or more processors, a contrast medium through a catheter so as to generate data indicative of a pressure of the contrast medium versus time;
   injecting, under the control of the one or more processors, a simulated contrast medium through the catheter so as to generate data indicative of a pressure of the simulated contrast medium versus time, wherein the simulated contrast medium includes a simulated contrast agent and a diluent;
   comparing, by the one or more processors, the pressure of the contrast medium to the pressure of the simulated contrast medium; and
   adjusting a concentration of the simulated contrast agent in the simulated contrast medium based on the comparison.

2. The method of claim 1, wherein comparing the pressure of the contrast medium to the pressure of the simulated contrast medium comprises determining a difference between a maximum pressure of the contrast medium during injection and a maximum pressure of the simulated contrast medium during injection.

3. The method of claim 1, wherein comparing the pressure of the contrast medium to the pressure of the simulated contrast medium comprises determining a difference between an average pressure of the contrast medium and an average pressure of the simulated contrast medium.

4. The method of claim 3, wherein the average pressure of the contrast medium is a mean pressure of the contrast medium discharged from an injection device during injection, and the average pressure of the simulated contrast medium is a mean pressure of the simulated contrast medium discharged from the injection device during injection.

5. The method of claim 1, wherein adjusting the concentration of the simulated contrast agent in the simulated contrast medium based on the comparison comprises one of increasing the concentration of the simulated contrast agent in the simulated contrast medium by adding additional simulated contrast agent and decreasing the concentration of the simulated contrast agent in the simulated contrast medium by adding additional diluent.

6. The method of claim 1, wherein adjusting the concentration of the simulated contrast agent comprising adjusting the concentration of the simulated contrast agent until a profile of pressure versus time for the simulated contrast medium is substantially the same as a profile of pressure versus time for the contrast medium.

7. The method of claim 6, wherein adjusting the concentration of the simulated contrast agent comprises one of increasing the concentration of the simulated contrast agent in the simulated contrast medium and decreasing the concentration of the simulated contrast agent in the simulated contrast medium until the profile of pressure versus time measured during injection for the simulated contrast medium is substantially the same as the profile of pressure versus time measured during injection of the contrast medium.

8. The method of claim 1, wherein the simulated contrast agent comprises a polymer.

9. The method of claim 8, wherein the polymer ranges from approximately 0.1 weight percent to approximately 10 weight percent of the simulated contrast medium.

10. The method of claim 9, wherein the polymer ranges from approximately 1 weight percent to approximately 5 weight percent of the simulated contrast medium.

11. The method of claim 8, wherein the diluent comprises water.

12. The method of claim 1, wherein the simulated contrast agent comprises at least one of polyvinyl alcohol, polyethylene glycol, and starch.

13. The method of claim 1, wherein simulated contrast agent comprises polyvinyl alcohol and the diluent comprises water.

14. The method of claim 1, wherein the simulated contrast medium exhibits thixotropic behavior.

15. The method of claim 1, wherein the contrast medium comprises iodine and the simulated contrast medium is devoid of iodine.

16. The method of claim 1, wherein injecting the simulated contrast medium comprises injecting the simulated contrast medium into a waste reservoir.

17. The method of claim 1, wherein injecting, under the control of one or more processors, the contrast medium through the catheter comprises injecting the contrast medium from a syringe containing the contrast medium installed on a contrast injection system; and
   wherein injecting, under the control of the one or more processors, the simulated contrast medium through the catheter comprising injecting the simulated contrast medium from a syringe containing the simulated contrast medium installed on the contrast injection system.

18. The method of claim 17, wherein generating the data indicative of the pressure of the contrast medium versus time comprises measuring the pressure of the contrast medium during injection via a pressure sensor of the contrast injection system, and generating the data indicative of the pressure of the simulated contrast medium versus time comprises measuring the pressure of the simulated contrast medium during injection via the pressure sensor of the contrast injection system.

19. The method of claim 1, wherein the data indicative of the pressure of the contrast medium versus time comprises data indicative of the pressure of the contrast medium in the catheter during injection, and the data indicative of the pressure of the simulated contrast medium versus time comprises data indicative of the pressure of the simulated contrast medium in the catheter during injection.

20. The method of claim 1, wherein the data indicative of the pressure of the contrast medium versus time comprises a measure of the pressure of the contrast medium from a time when a plunger of a contrast injection system begins advancing inside a syringe containing the contrast medium and a time when the plunger stops advancing inside the syringe containing the contrast medium, and wherein the data indicative of the pressure of the simulated contrast medium versus time comprises a measure of the pressure of the simulated contrast medium from a time when the plunger of the contrast injection system begins advancing inside a syringe containing the simulated contrast medium and a time when the plunger stops advancing inside the syringe containing the simulated contrast medium.

* * * * *